United States Patent [19]

Chevallet

[11] Patent Number: 5,043,074
[45] Date of Patent: Aug. 27, 1991

[54] DEVICE AND METHOD FOR MEASURING THE ULTRAFILTRATION IN AN ARTIFICIAL KIDNEY

[75] Inventor: Jacques Chevallet, Serezin du Rhone, France

[73] Assignee: Hospal Industrie, Cedex, France

[21] Appl. No.: 531,764

[22] Filed: Jun. 1, 1990

[30] Foreign Application Priority Data

Jun. 2, 1989 [FR] France .................. 89 07567

[51] Int. Cl.⁵ .................................... B01D 61/34
[52] U.S. Cl. ...................... 210/646; 210/744; 210/750; 210/97; 210/143; 210/188; 210/321.65; 210/472; 210/929; 73/219; 73/223
[58] Field of Search ............... 210/646, 647, 744, 750, 210/97, 143, 188, 321.65, 472, 929; 73/3, 219, 223

[56] References Cited

U.S. PATENT DOCUMENTS

| | | | |
|---|---|---|---|
| 1,699,562 | 1/1929 | Courtioux ...................... | 73/219 |
| 1,846,852 | 2/1932 | Dubreuil ...................... | 73/219 |
| 1,962,192 | 6/1934 | Hapgood ...................... | 73/219 |
| 2,964,944 | 12/1960 | Kuntz ............................ | 73/219 |
| 3,669,880 | 6/1972 | Marantz et al. .............. | 210/321.65 |
| 3,939,069 | 2/1976 | Granger et al. .............. | 210/321.65 |
| 3,979,284 | 9/1976 | Granger et al. .............. | 210/321.65 |
| 4,267,041 | 5/1981 | Schael .......................... | 210/321.65 |
| 4,530,465 | 7/1985 | Gauchet et al. .............. | 73/223 |
| 4,767,526 | 8/1988 | Vantard ........................ | 210/321.65 |
| 4,857,199 | 9/1989 | Cortial ......................... | 210/929 |
| 4,859,319 | 8/1989 | Borsari ......................... | 210/86 |

FOREIGN PATENT DOCUMENTS

0213050A1 4/1987 European Pat. Off. .

Primary Examiner—W. Gary Jones
Attorney, Agent, or Firm—Finnegan, Henderson, Farabow, Garrett & Dunner

[57] ABSTRACT

The invention includes a device for measuring a quantity of liquid extracted from a dialysis liquid circuit, the device having a reservoir means connected to the dialysis liquid circuit for receiving liquid from the dialysis liquid circuit, at least one measurement container for receiving liquid from the reservoir, a flow channel connecting the reservoir with the at least one measurement container for selectively filling the measurement container with liquid from the reservoir, a level detector disposed proximate a predetermined area on the at least one measurement container for detecting the presence of liquid at a predetermined level, and a drain port on the measurement container for receiving a signal from the level detector to empty the contents of the measurement container after the presence of liquid at the predetermined level is detected. The invention also includes a method for measuring a quantity of liquid extracted from an artificial kidney in a dialysis liquid circuit including the steps of successively filling a measurement container to a predetermined level with liquid to be measured, emptying the measurement container, reducing the rate of filling of the measurement container as the predetermined level is approached, and detecting the presence of liquid at the predetermined level.

21 Claims, 1 Drawing Sheet

DEVICE AND METHOD FOR MEASURING THE ULTRAFILTRATION IN AN ARTIFICIAL KIDNEY

BACKGROUND OF THE INVENTION

1. Field of the Invention

The present invention relates to the technical field of extracorporeal treatment of blood by an artificial kidney. More particularly, the present invention relates to a device and a method for measuring the ultrafiltration quantity.

2. Description of the Related Art

Patent Application No. EP 213,050 describes a device that permits measurement of the ultrafiltration of blood by measuring the quantity of liquid extracted from the dialysis liquid circuit by an ultrafiltration pump. The device consists essentially of two containers each having a measurement probe capable of indicating when a predetermined level is reached in each of the containers. Each container is filled with liquid pumped by a pump. A set of valves, controlled by a control element are arranged to fill one container while simultaneously emptying the other container, and vice versa. The probes send an electrical signal to the control element each time the predetermined level is reached, and the control element, knowing the volume of each container, can then calculate the quantity of ultrafiltrated liquid. However, a drawback to the above-identified device is that it lacks precision in situations where the pumped liquid contains bubbles. Such bubbles interfere with level detection by the measurement probes.

In addition, the above-described device loses precision as the filling rate of the containers increases. In situations where the measured liquid is conveyed by a pulsed ultrafiltration pump, liquid level detection is disturbed.

An object of the present invention is to overcome the disadvantages of the prior art and to provide a device and a method for measuring ultrafiltrate that eliminates the presence of bubbles in the liquid extracted the dialysis liquid circuit.

Another object of the present invention is to provide a device and a method for measuring the ultrafiltrate which are not as sensitive to pulsations in the liquid being measured.

A further object of the present invention is to provide a device and a method for measuring ultrafiltrate wherein the filling rate of the containers can be reduced as the liquid approaches the level-detection devices.

SUMMARY OF THE INVENTION

In order to achieve these objects, the present invention provides a device for measuring, in an artificial kidney, the quantity of liquid extracted from the dialysis liquid circuit and corresponding to the ultrafiltration of the blood, including at least one measurement container intended to receive the extracted liquid, the container being provided with at least one level-detector capable of detecting the presence of liquid at a predetermined level.

The device also includes means for emptying the measurement container, including at least one buffer container connected on one end to the dialysis liquid circuit and connected on the other end to the measurement container to provide for its filling. A buffer container is located so that it is possible to fill said measurement container by gravity from the buffer container.

The present invention also relates to a method for measuring, in an artificial kidney, the quantity of liquid extracted from the dialysis liquid circuit and corresponding to the ultrafiltration of the blood. The method includes the steps of successively filling and emptying at least one measurement container with the liquid to be measured, detecting the presence of liquid at a predetermined level in the container, and reducing the rate of filling of the measurement container as the predetermined level is approached.

Additional objects and advantage of the invention will be set forth in part in the description which follows, and in part will be obvious from the description, or may be learned by practice of the invention. The objects and advantages of the invention will be realized and attained by means of the elements and combinations particularly pointed out in the appended claims.

DESCRIPTION OF THE PREFERRED EMBODIMENTS

Figure 1:
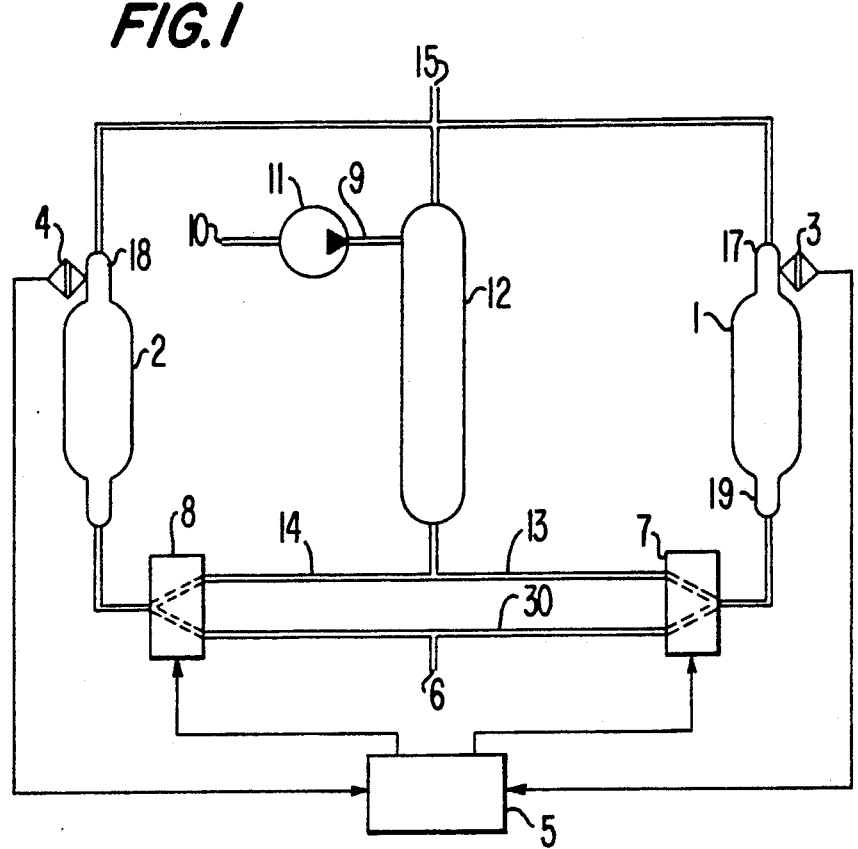
FIG. 1 is a schematic diagram of a measuring device in accordance with a first embodiment of the present invention.

In accordance with the invention, the measuring device includes a first measurement container 1 and a second measurement container 2 consisting of, for example, vertical cylindrical reservoirs. The containers are each provided at their upper end with vertical tubes having reduced cross-sections, around which there are arranged level-detectors 3 and 4 connected to control element 5.

The lower ends of the containers 1 and 2 are connected to selectively communicate with either a source of the liquid to be measured or with discharge means 6, through three-way valves 7 and 8. Discharge means 6 may include a drain. Preferably, valves 7 and 8 are solenoid valves controlled by control element 5.

In operation, the liquid to be measured flows from dialysis liquid circuit 10, through channel 9 into reservoir 12. The liquid can be made to circulate into reservoir 12, through channel 9, by any appropriate means, such as ultrafiltration pump 11.

Reservoir 12 can be of the same type as containers 1 and 2, and is connected to circuit 10 via pump 11 by way of channel 9. Channel 9 preferably is connected to the upper end of reservoir 12.

The lower end of reservoir 12 is connected via channel 13 to valve 7 for establishing communication between reservoir 12 and measurement container 1. Reservoir 12 also is connected via channel 14 to valve 8 for establishing communication between reservoir 12 and measurement container 2. The three containers 1, 2 and 12 are advantageously connected via an appropriate device 15 (not shown) to atmospheric pressure.

By way of example and not limitation, a function of the measuring device will now be described in connection with the measurement of ultrafiltrate from the blood. First, ultrafiltrate coming from dialysis liquid circuit 10 is pumped by pump 11 through channel 9 into reservoir 12. Reservoir 12 is opened to the atmosphere to de-gas the ultrafiltrate withdrawn from the dialysis liquid circuit. This de-gassing is further promoted by the fact that reservoir 12 is fed with liquid to be measured via its upper end. Thus, when the liquid extracted by pump 11 contains bubbles, the de-gassing that occurs prevents bubbles from interfering with level-detection by detectors 3 and 4. Container 1 is filled with fluid from reservoir 12 when valve 7 is adjusted to allow fluid communication between channel 13 and container 1. During the filling operation of container 1, valve 8 is adjusted to block fluid communication between reservoir 12 and container 2, and to allow fluid communication between container 2 and discharge means 6. Container 1 is simultaneously filled with reservoir 12. However, the filling of reservoir 12 may occur at a slower rate, depending on the ultrafiltration flow rate, (i.e., the extraction of the liquid through the channel 9).

When the liquid in container 1 reaches level detector 3, level detector 3 transmits an electrical signal to control element 5 which calculates the liquid volume base on the known capacity of container 1 and the capacity of various liquid channels. Element 5 also may include a display device for displaying the volume. The electrical signal transmitted by detector 3 to element 5 also triggers element 5 to adjust valves 7 and 8 to block fluid communication between container 1 and reservoir 12 and to establish flow communication between container 1, and discharge means 6. The electrical signal from element 3 also triggers element 5 to block flow communication between container 2 and discharge means 6, and to establish fluid communication between container 2 and reservoir 12. Container 1 will then be in the emptying phase and container 2 will be in the filling phase.

Container 2 initially is filled with liquid already present in the buffer reservoir 12. This liquid flows by gravity, according to principles of communicating vessels, at a fairly rapid rate. In contrast, the end of the filling phase may occur slowly depending upon the ultrafiltration flow rate. Indeed, the rise of the liquid in measurement container 2 takes place in parallel with the rise of the liquid in reservoir 12. Thus, because reservoir 12 has a large cross-section, as the liquid level approaches the level of detectors 3 and 4, the final rate of filling will be slow, even though detectors 3 and 4 are positioned on narrow channels 17 and 18, respectively, at the top ends of containers 1 and 2. The narrow cross-section of channels 17 and 18, in which the liquid circulates at the time of detection, affords highly accurate volumetric measurement. In addition, the slow filling rate affords accurate level detection. When the liquid reaches the level of detector 4, detector 4 emits an electrical signal which is transmitted to element 5. This causes element 5 to reverse the opening of valve 7 to fill container 1 and the closing of valve 8 to drain container 2. In addition, element 5, knowing the capacity of the container 2, will increment the value of the ultrafiltration measured by the volume of container 2. This new ultrafiltration value can then be displayed. The measuring device described above continues to alternately fill and empty each container. While one of the containers is in the emptying phase, the other is in the filling phase, and vice versa.

The slow rise of the liquid at the end of each filling phase advantageously affords precise level detection. In addition, since reservoir 12 is opened to the atmosphere and is supplied with liquid via its upper end, it is possible to effectively degas the liquid to be measured. This prevents measurement errors arising from poor detection caused by the bubbles interfering with level detectors 3 and 4. Reservoir 12 also constitutes a sort of buffer for attenuating disturbances which may originate from the possible pulsations of ultrafiltration pump 11.

Tests carried out with a measuring device of the present invention have made it possible to perform measurements with a precision of one per thousand.

The measuring device of the present invention is described above as having three-way valves 7 and 8. However, the function of valves 7 and 8 can be replicated with combinations of other types of valves. For example, each of valves 7 and 8 can be replaced with two two-way valves.

The respective capacities of measurement containers 1 and 2 do not constitute a critical factor of the present invention. However, given, that updated volume information is only possible upon each new filling of a measurement container, and given that it is desirable to provide information as frequently as possible, it is preferable to have containers of low capacity. On the other hand, each switching of valves 7 and 8 results in an error, however small, in the measurement carried out. In order to reduce this error as much as possible, it is desirable to reduce the number of switchings and to provide containers of large capacity. The choice of the capacity of the containers is therefore a trade-off between these two demands, and it has been found that capacity on the order of 20 ml is satisfactory.

Further, containers 1 and 2 may or may not have equal capacity, and their calibration can be effected by any known means. For example, it is possible to calibrate each one of the measurement containers individually, or simply calibrate them both together. In the latter case, if the two containers are approximately of the same capacity, the value of the calibration can be divided by two in order to provide control element 5 with the filling value of each of the containers. This allows ultrafiltration to be incremented upon each new filling of containers 1 or 2. It is also possible to increment the value of ultrafiltration only upon each new filling of the two containers. For example, each time container 1 is filled, the value of the ultrafiltration is incremented by element 5 in an amount equal to the capacity of the two containers.

The shape of reservoir 12 can also be the subject of a large number of alternative embodiments. The advantageous characteristic of reservoir 12, however, is that it has a large cross-section at the level of detectors 3 and 4 in order to reduce the filling rate at the end of filling of containers 1 and 2.

As has been described, the liquid to be measured is introduced at the upper end of reservoir 12, which is advantageous in ensuring sufficient degassing. However, it is possible to feed reservoir 12 at any level, and to ensure the degassing of the liquid to be measured by means of a specific device upstream of the measuring device.

The measuring device according to the present invention has been described as having two measurement containers (1, 2) for receiving the liquid extracted from the dialysis liquid circuit.

Figure 2:
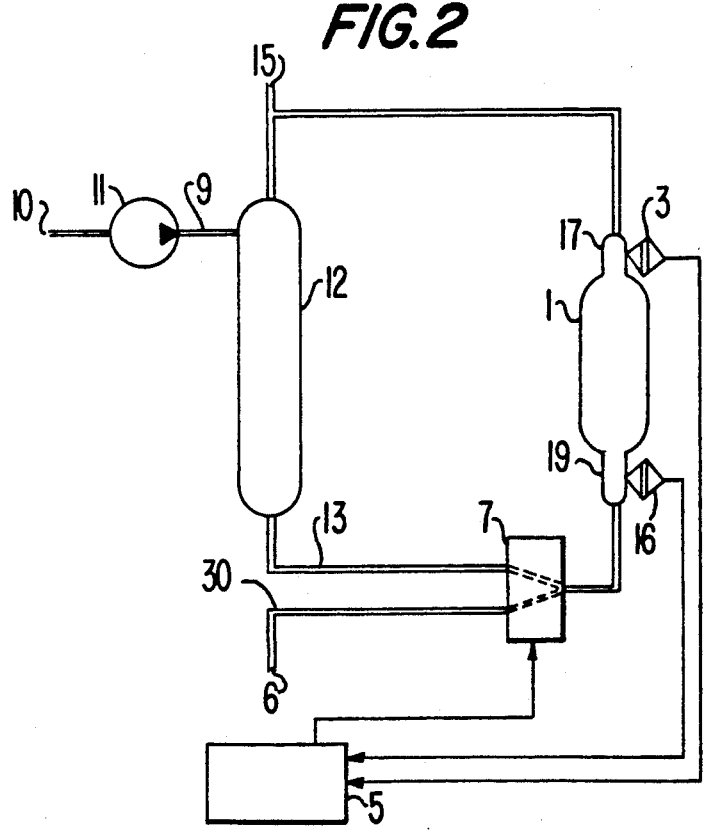
FIG. 2 is a schematic diagram of a measuring device in accordance with a second embodiment of the present invention.

However, this device can function with a larger number of containers, for successive filling and emptying. It can also be used, in certain cases, such as where the ultrafiltration flow rate is low, with a single container for measuring the extracted liquid. This embodiment is illustrated in FIG. 2, wherein elements identical to those shown in FIG. 1 are identified by the same reference numerals. In the second embodiment reservoir 12 must have a capacity sufficient to serve as a buffer for liquid from dialysis circuit 10 during the emptying phase of container 1.

The second embodiment functions as follows. First, pump 11 pumps ultrafiltrate from dialysis liquid circuit 10 to reservoir 12 where it is de-gassed. The liquid is then transferred to measurement container 1 which fills until the liquid reaches the level of detector 3. When this occurs control element 5 switches valve 7 to close channel 13 between reservoir 12 and container 1, and to open channel 30 between container 1 and emptying means 6, thereby emptying container 1.

During this emptying period, the liquid extracted by pump 11 accumulates in reservoir 12 and then, when container 1 is emptied, the control element 5 switches valve 7 to close channel 30 between measurement container 1 and emptying means 6 and to establish flow communication in channel 13 between reservoir 12 and container 1.

Container 1 then fills from reservoir 12, first rapidly, and then more slowly as the liquid approaches the level of detector 3. Information relating to the emptied state of container 1 can be transmitted to control element 5 by means of a low-level detector 16 disposed at bottom end 19 of container 1.

Other embodiments of the invention will be apparent to those skilled in the art from consideration of the specification and practice of the invention as disclosed herein. It is intended that the specification and examples be considered as exemplary only, with the true scope and spirit of the invention being indicated by the following claims.

What is claimed is:

1. A device for measuring a quantity of liquid extracted from a dialysis liquid circuit, the device comprising:
   reservoir means connected to the dialysis liquid circuit for receiving liquid from the dialysis liquid circuit;
   at least one measurement container for receiving liquid from said reservoir means;
   means connecting said reservoir means with said at least one measurement container for selectively filling said measurement container with liquid from said reservoir means;
   level detection means disposed proximate a predetermined area on said at least one measurement container for detecting the presence of liquid at a predetermined level; and
   emptying means connected to said at least one measurement container for receiving a signal when said level detection means detects the presence of liquid at said predetermined level to empty the contents of said at least one measurement container.

2. A device as set forth in claim 1 wherein said reservoir means and said at least one measurement container are disposed to allow liquid in said reservoir means to flow via gravity to said at least one measurement container.

3. A device as set forth in claim 1 wherein said at least one measurement container includes two measurement containers, and wherein said connecting means includes valve means for selectively and alternately filling each of said measurement containers from said reservoir means.

4. A device as set forth in claim 1 wherein at least one of said reservoir means and said at least one measurement container is connected to a source of atmospheric pressure.

5. A device as set forth in claim 1 wherein said at least one measurement container has an upper portion and a mid-portion, a cross-sectional area of said upper portion being smaller than a cross-sectional area of said mid-portion, said level detection means being disposed proximate said upper portion.

6. A device as set forth in claim 1 wherein said reservoir means includes a portion disposed at the level of said detection means, said portion of said reservoir means having a cross-sectional area being greater than or equal to a cross-sectional area of said measurement container at the level of said detection means.

7. A device as set forth in claim 1 wherein said reservoir means includes an upper end and a lower end, the dialysis liquid circuit being connected to said reservoir means proximate said upper end.

8. A device as set forth in claim 1 wherein said reservoir means includes an upper end and a lower end, said connecting means being connected to said reservoir means proximate said lower end.

9. A device as set forth in claim 1 wherein said connecting means includes valve means for selectively filling and emptying said at least one measurement container, said valve means responsive to a signal when said level detecting means detects the presence of liquid at said predetermined level, to discharge the contents of said at least one measurement container.

10. A device as set forth in claim 9 wherein said valve means includes a three-way valve.

11. A device as set forth in claim 9 further including control means for receiving signals from said detecting means to control said valve means.

12. A device as set forth in claim 11 wherein said valve means is adjustable between a first position and a second position, wherein in said first position a flow path between said reservoir means and said at least one container is opened and a flow path between said at least one container and a drain is closed, and wherein in said second position a flow path between said reservoir means and said at least one container is closed and a flow path between said at least one container and a drain is opened.

13. A device as set forth in claim 1, wherein the quantity of liquid extracted from the dialysis liquid circuit is equal to a quantity of liquid ultrafiltrated from the blood.

14. A device for measuring a quantity of liquid extracted from a dialysis liquid circuit, the device comprising:
   a reservoir having a top end and a bottom end and being connected to said dialysis liquid circuit proximate said top end, said top end including an opening for exposing the contents of said reservoir to the atmosphere;
   at least one measurement container having a top end, a bottom end and a mid-portion disposed between said top and bottom ends, said top end having a cross-sectional area being less than a cross-sectional area of said mid-portion;
   a flow channel connecting the bottom ends of said reservoir and said at least one measurement container;
   high level detection means disposed proximate the top end of said at least one measurement container for detecting the presence of liquid at a predetermined position;
   valve means for regulating liquid flow to and from said at least one measurement container, said valve means being disposed in-line with said flow channel and moveable between a first position permitting fluid flow between said reservoir and said measurement container and obstructing fluid flow from said measurement container to a drain, and a second position permitting fluid flow from said measurement container to a drain and obstructing fluid flow from said reservoir to said measurement container; and control means for receiving a detection signal from said level detection means and for controlling said valve means based upon said detection signal.

15. A device as set forth in claim 14 further including a low level detector disposed proximate the bottom end of said at least one measurement container for sending a signal to said control means, said control means for changing the position of said valve means from said second position to said first position upon detection of said signal from said low level detector.

16. A method for measuring a quantity of liquid extracted from a dialysis liquid circuit of an artificial kidney, the method comprising the steps of:

successively filling at least one measurement container to a predetermined level with liquid to be measured and emptying said measurement container;

reducing the rate of filling of said measurement container as said predetermined level is approached; and detecting the presence of liquid at said predetermined level.

17. A method as set forth in claim 16 further including the step of collecting liquid to be measured in a reservoir prior to filling said at least one measurement container.

18. A method as set forth in claim 17 wherein the step of filling at least one measurement container includes successively filling by gravity from said reservoir a first measurement container and emptying the first measurement container to a drain, and filling by gravity from the reservoir a second measurement container, and emptying the second measurement container.

19. A method as set forth in claim 16 further including the step of degassing the liquid to be measured before filling said at least one measurement container.

20. A method as set forth in claim 16 including the step of controlling at least one three-way valve to alternately fill and empty said at least one measurement container.

21. A method as set forth in claim 16, wherein said quantity of liquid extracted from the dialysis liquid circuit is equal to a quantity of liquid ultrafiltrated from the blood.

* * * * *